United States Patent [19]

Gits

[11] 4,008,317
[45] Feb. 15, 1977

[54] VARICELLA-ZOSTER VIRUS VACCINE AND PREPARATION THEREOF

[75] Inventor: Jacqueline Gits, La Hulpe, Belgium

[73] Assignee: Recherche et Industrie Therapeutiques (R.I.T.), Belgium

[22] Filed: Dec. 29, 1975

[21] Appl. No.: 644,787

[52] U.S. Cl. .................................. 424/89; 195/1.4; 195/1.8
[51] Int. Cl.² ...................................... A61K 39/12
[58] Field of Search ............... 424/89; 195/1.8, 1.4.

[56] References Cited
OTHER PUBLICATIONS

Ledinko et al., —Chem. Abst., vol. 80, (1974), p. 56297w.
Casto et al.,—Chem. Abst., vol. 81, (1974), p. 22072z.

*Primary Examiner*—Sam Rosen
*Attorney, Agent, or Firm*—Alan D. Lourie; William H. Edgerton

[57] ABSTRACT

Non-pathogenic varicella-zoster virus mutants are obtained by induction and isolation of temperature-sensitive mutant strains. N-methyl-N'-nitro-N-nitrosoguanidine is employed as mutagenic agent. The obtained mutants are useful for vaccine production.

6 Claims, No Drawings

VARICELLA-ZOSTER VIRUS VACCINE AND PREPARATION THEREOF

The present invention relates to novel varicella-zoster virus vaccines and to the process for preparing them.

Varicella is a common and highly contagious disease, chiefly of children. Although varicella is a mild disease, complications —e.g. encephalitis— does at times occur : in neonatal varicella the mortality may be as high as 20 % and in the adult infections, the disease is more severe and the mortality may be as high as 20 %. It is estimated that in varicella encephalitis, mortality level reaches about 10 % and another 10 % survive with severe injury to the central nervous system.

Herpes zoster is the recurrent form of the disease, occuring in adults who were previously infected with the varicella-zoster virus and, in addition to the pathology of varicella, an inflammatory reaction of the dorsal nerve roots and ganglia may occur.

If the inflammation spreads into the spinal cord or cranial nerves paralysis results.

The increased dangers of varicella-zoster in immunodepressed human beings or in those undergoing immunosuppressive treatment are now well documented —e.g. by Gerskon A. et al. in J. Pediat. 81 : 1034, Nov. 1972 and by Schaison G. et al. in Actual. Hematol. 6 (5) : 112–22, 1971.

Prevention or modification of the disease by passive immunization with gammaglobulins (Ross A. H., New Engl. J. Med. 267 : 369–76, 1962), zoster immune globulin (Z.I.G.) (Brunnel P. A. et al., New Engl. J. Med. 280 : 1191–94, 1969) or by administration of cytosine arabinoside (Stevens D. A. et al., New Engl. J. Med. 289 : 873–78, 1973) is known. Nevertheless, in clinical practice, active immunization remains the best approach for the threatened groups and live attenuated varicella vaccines have already been described (Belgian patent No. 766,333; Iovlev V. I. in Vopr. Virusol. 5 : 561, 1969; Takahashi M. et al. in Lancet II (7892) : 1288–90, 1974). Each of these vaccines is a live vaccine containing varicella virus attenuated by serial passages in particular tissue culture or cultures.

Nevertheless, the use of a varicella live virus vaccine does not avoid the risk of possible recurrence of the illness as indicated hereinabove and a present problem in varicella virus vaccine development is to minimize this risk.

The present invention is based on the concept of temperature-sensitive mutant and describes a process for preparing new live varicella vaccines which contain a temperature-sensitive (ts) varicella virus mutant.

By the term "temperature-sensitive mutant" it is understood a modified virus strain, the growing capacity of which is substantially inhibited at temperatures above its cut-off temperature while replication of the wild strain remains substantially unaffected at that temperature. In the best conditions, a ts mutant with a cut-off temperature —i.e. the lower temperature at which the replication of the ts strain is reduced of at least 2 $\log_{10}$ versus virus replication at usual temperature— in the range of the normal body temperature should be able to multiply in a cold mucosa or in the skin while its replication should be inhibited in the body.

The phenomenon has been applied to the development of some live virus vaccine (Murphy B. R. et al., J. Infect. Dis. 162 (2) : 170, Aug. 1972; Belgian patents Nos. 808,708; 812,816; and 814,632) but no ts varicella-zoster virus vaccine has been described to date.

It is the object of the present invention to provide varicella-zoster ts viruses which, upon inoculation into the skin, substantially grow only at the site of injection where the temperature is several degrees lower than in the internal parts of the body. We have demonstrated that, by stimulating the immunologic system of the subject, such a ts varicella-zoster virus vaccine does induce varicella antibodies.

A further interest of the varicella virus vaccine of the present invention resides in their potential ability to prevent varicella-zoster virus reactivation. It is important indeed to counteract the gradual decline of the initial antibody level with advancing age which permits virus reactivation, multiplication and spreading along the sensory nerve which causes herpes zoster.

The present invention thus relates to live varicella-zoster virus vaccine comprising an effective dose of a temperature-sensitive N-methyl-N'-nitro-N-nitrosoguanidine induced mutant of a pathogenic varicella-zoster virus, said mutant having a cut-off temperature of about 37° C and being able to multiply in the dermic tissue but having inhibited replication in the internal organs, and a pharmaceutical diluent, e.g. for intradermic administration.

The vaccine is preferably presented in freeze-dried form.

The process of preparing a ts and non-pathogenic varicella-zoster virus mutant valuable for vaccinal use or vaccine preparation according to this invention consists in bringing a cell-free varicella-zoster virus strain into contact with an aqueous solution of N-methyl-N'-nitro-N-nitrosoguanidine (NTG) —e.g. at a concentration of 100 μg per milliliter and for 2 hours- at room temperature (i.e. between 18° and 25° C), inoculating the surviving virus population into a tissue culture known to the art for accepting growth of varicella-zoster virus and acceptable as substrate for vaccine production, at a temperature comprised between 30° and 35° C, harvesting the virus —preferably after disrupting the cells, e.g. by sonication—, isolating the harvested virus mutant —e.g. by cloning it by end-point dilution at a temperature comprised between 28° and 35° C, e.g. 30° C— and isolating the adequate ts mutant by parallel culture at a permissive and a non-permissive temperature —e.g. 30° and 37.5° C respectively.

In the above process, it is obvious that NTG concentration and contact period are interrelated but the operative conditions are such that the mutagenic treatment involves a mortality of about 90% of the virus population.

Examples of tissue cultures accepting growth of varicella-zoster virus and acceptable as substrate for vaccine preparation are human embryonic lung (HEL) cells, more particularly Wi-38 cell line.

For vaccine use or production, a varicella-zoster virus ts mutant strain isolated as hereinabove described is further passaged in a tissue culture known to the art for accepting growth of varicella-zoster virus and acceptable as substrate for vaccine production to get a substantial amount of said ts mutant strain, using therefore any technique known to the art for vaccine production and stabilization.

The so-obtained live varicella-zoster virus vaccine is administered by a cold route —and preferably by intradermic route— to a susceptible organism.

The following examples illustrate the invention starting from a pathogenic strain of varicella-zoster virus which has been deposited at the WHO collaborating Centre for Collection and Evaluation of Data on Comparative Virology at the Institut fur Medizinische Mikrobiologie, Infektions- und Seuchenmedizin der Ludwig-Maximilians Universitat (Munich, Germany) where it received accession number P/75/1.

A varicella-zoster virus mutant strain obtained from the P/75/1 strain by the hereinabove described process has also been deposited at the same WHO collaborating Centre for Collection und Evaluation of Data on Comparative Virology where it received accession number P/75/2.

This mutant strain is temperature-sensitive and non-pathogenic and valuable for varicella-zoster virus vaccine use or production. It is obvious that the examplification is not limitative of the invention.

EXAMPLE 1

Varicella-zoster virus P/75/1 isolated from the vesicle fluid of an infected child is passaged six times in Wi-38 cell cultures. The cells are harvested with ice-cooled sodium edetate aqueous solution and sonicated during 30 seconds at the highest power of a Branson Europa Sonicator, model J 22 (Branson Europa N.V., Soest, The Netherlands) in SPGE buffered solution consisting of sucrose (0.218 M); potassium phosphate monobasic (0.0038 M); sodium phosphate dibasic (0.0072 M); monopotassium glutamate (0.0049 M) and sodium edetate (0.2 %) in water; supplemented with polyvinyl pyrrolidone (PVP) K 15 (molecular weight 10,000) up to a final concentration of 1%(w/v). The supernatant is filtered on 3 μm Millipore filter. An aliquot of this cell-free virus is maintained for two hours in contact with an aqueous NTG solution dissolved in Eagle's basal medium (final concentration : 100 μg/ml) and adsorbed on Wi-38 cells for 30 minutes. The infected culture is then washed three times with Eagle's basal medium and incubated for 3 days at 30° C. The virus is harvested as hereabove described and the cell-free virus is stored at −70° C up to the following step.

The cell-free virus is cloned by end-point dilution in Wi-38 cells (2.10$^5$ cells/tube) incubated at 30° C. Cytopathogenic effects (CPE) appear 4 to 10 days later in less than one out of five tubes and with no more than one plaque per infected tube. The viruses isolated from said plaques are harvested and inoculated into parallel cultures, incubated at 30° and 37.5° C respectively.

The clones which produce no CPE at 37.5° C but which produce CPE at 30° C are considered as ts mutants.

EXAMPLE 2

One of the varicella-zoster virus ts strains obtained in example 1 and labelled P/75/2 is cultivated in Wi-38 cells for 3 days at 30° C and then harvested as hereabove described in example 1, distributed in two ml. glass vials containing at least 10,000 Pfu/dose and freeze-dried for constituting dosage units of varicella-zoster virus vaccine.

EXAMPLE 3

Ts character of varicella-zoster virus strain P/75/2.

Virus production at different temperatures on Wi-38 cell line has been determined and the results are summarized in following Tables 1 and 2.

TABLE 1

| Days after incubation | Virus yield of cell-associated virus per inoculated flask(x) at various temperatures | | | | |
|---|---|---|---|---|---|
| | 30° C | 35° C | 36° C | 37° C | 38° C |
| 2 | 750(xx) | 730 | 350 | 10 | 1 |
| 3 | 1,600 | 3,300 | 250 | 0 | 0 |
| 4 | 4,500 | 5,400 | 690 | 0 | 0 |
| 5 | 5,800 | 1,500 | 700 | 0 | 0 |
| 6 | 6,300 | 1,200 | 500 | 0 | 0 |

(x)inoculum = 100 p.f.u. of cell-associated virus per flask
(xx)expressed as plaque forming unit (p.f.u.) per 0.1 ml.

TABLE 2

| Virus yield of cell-free virus at various temperatures | | | |
|---|---|---|---|
| Inoculum | Days after incubation | 35° C | 37° C |
| 80p.f.u./10$^6$ cells | 3 | 500(x) | 0 |
| | 4 | 2,050 | 0 |
| | 5 | 5,600 | 0 |
| | 6 | 3,800 | 0 |
| 2,000p.f.u./10$^6$ cells | 3 | 17,100 | 11 |
| | 4 | 16,000 | 5 |
| | 5 | 5,000 | 0 |
| | 6 | 800 | 0 |

(x)expressed as p.f.u. per 0.1 ml.

The results indicate a cut-off temperature of 37° C for the cell-associated virus (Table 1) as well as for the cell-free virus (Table 2).

Thermostability of the ts varicella zoster virus mutant P/75/2.

To test the thermostability of the ts varicella-zoster virus P/75/2, samples of cell-free virus were kept for 0, 10, 30 or 60 minutes at a non-permissive temperature (37° C) before being inoculated into Wi-38 cells which were then incubated at the permissive temperature of 35° C for 4 days.

The following Table 3 summarizes the results for the pathogenic strain P/75/1 and for the ts mutant P/75/2.

TABLE 3

| Thermal inactivation of P/75/1 and P/75/2 strains at 37° C | | |
|---|---|---|
| Duration of exposure at 37° C | Infective titer of 0.1 ml. viral suspension | |
| | P/75/1 | P/75/2 |
| 0 | 1,500(x) | 1,160 |
| 10 minutes | 1,250 | 920 |
| 30 minutes | 600 | 400 |
| 60 minutes | 400 | 255 |

(x)expressed as p.f.u. per 0.1 ml.

As indicated in Table 3, the pathogenic virus P/75/1 and the ts strain P/75/2 show similar thermostability.

EXAMPLE 4

Clinical and serological results

It is known that chimpanzees (Pan Trogoldytes) are susceptible to varicella zoster infections (Henschele WP, JAVMA 136 (6) : 256–57, 1960) and, therefore, three of these animals were used for clinical and serological tests of the P/75/2 mutant.

The animals were inoculated intradermally in the right forearm with 30,000 p.f.u. (0.5 ml.) of the vaccine of the example 2.

For each animal, 0.5 ml. of a placebo composition (SPGE/PVP K15) was injected in the left leg.

Rectal temperature and clinical status were recorded on day 3, 14, 21 and 28 post inoculation (p.i.).

Absence of clinical symptoms as well as of abnormal temperatures demonstrates the innocuity of the vaccine.

The immunogenicity of the P/75/2 mutant was assessed by seroneutralization and complement fixation tests, the result of which are given in Tables 4 and 5 respectively.

TABLE 4

| | Seroneutralization test Virus titer Day of bleeding after vaccination day | | | |
|---|---|---|---|---|
| Animal | 0 | 14 | 21 | 28 |
| 3 A | 16 | 64–128 | 64–128 | 128 |
| Manno | 16 | 128–256 | 128 | 64–128 |
| Jules | 512 | NT | 2048 | 2048 |

NT: not tested.

TABLE 5

| | Complement fixation test Day of bleeding p.i.: | | | |
|---|---|---|---|---|
| Animal | 0 | 14 | 21 | 28 |
| 3 A | <4 | 32 | 8 | 16 |
| Manno | <4 | 16 | 16 | 16 |
| Jules | <4 | 4–8 | 4–8 | 8 |

As indicated in Table 4, all animals were sero-positive prior to inoculation but had a four-fold increase in seroneutralization titers after vaccination.

Table 5 shows that all animals were negative by complement fixation test prior to vaccination but sero-converted 14 days after vaccination.

We claim:

1. A live varicella zoster virus vaccine comprising an effective dose of a temperature sensitive N-methyl-N'-nitro-N-nitrosoguanidine induced mutant strain of a pathogenic varicella-zoster virus, said strain having a cut-off temperature of 37° C and being able to multiply in the dermic tissue of a susceptible organism but having inhibited replication in the internal organs, and a pharmaceutical diluent.

2. A vaccine according to claim 1 in a form suitable for intradermic administration.

3. A vaccine according to claim 1, wherein the vaccine is freeze-dried.

4. A vaccine according to claim 1, wherein the temperature sensitive mutant strain is the P/75/2 strain.

5. A process of immunizing a susceptible organism against varicella and herpes zoster comprising administering to said organism an effective dose of a vaccine according to claim 1.

6. A process as claimed in claim 5 wherein the route of administration is intradermic.

* * * * *